(12) United States Patent
Pace

(10) Patent No.: US 9,539,305 B1
(45) Date of Patent: Jan. 10, 2017

(54) PRISTINAMYCIN COMPOSITIONS, LPXC COMPOSITIONS, THEIR IMPROVEMENTS, AND COMBINATIONS THEREOF

(71) Applicant: Fleurir ABX LLC, Raleigh, NC (US)

(72) Inventor: John Lee Pace, Cary, NC (US)

(73) Assignee: FLEURIR ABX LLC, Raleigh, NC (US)

( * ) Notice: Subject to any disclaimer, the term of this patent is extended or adjusted under 35 U.S.C. 154(b) by 0 days.

(21) Appl. No.: 14/659,609

(22) Filed: Mar. 16, 2015

Related U.S. Application Data

(60) Provisional application No. 61/953,721, filed on Mar. 14, 2014.

(51) Int. Cl.
| | | |
|---|---|---|
| *A61K 38/15* | (2006.01) | |
| *A61K 31/424* | (2006.01) | |
| *A61K 38/05* | (2006.01) | |
| *A61K 31/4164* | (2006.01) | |
| *A61K 31/166* | (2006.01) | |
| *A61K 38/06* | (2006.01) | |
| *A61K 45/06* | (2006.01) | |

(52) U.S. Cl.
CPC .............. *A61K 38/15* (2013.01); *A61K 31/166* (2013.01); *A61K 31/4164* (2013.01); *A61K 31/424* (2013.01); *A61K 38/05* (2013.01); *A61K 38/06* (2013.01); *A61K 45/06* (2013.01)

(58) Field of Classification Search
None
See application file for complete search history.

(56) References Cited

U.S. PATENT DOCUMENTS

| | | |
|---|---|---|
| 8,101,640 B2 | 1/2012 | Anderson et al. |
| 2004/0229955 A1* | 11/2004 | Andersen ............ C07C 233/83 514/616 |
| 2012/0283175 A1 | 11/2012 | Patten et al. |

FOREIGN PATENT DOCUMENTS

| | | |
|---|---|---|
| JP | 2014177468 | 9/2014 |
| WO | WO 2008154642 | 12/2008 |
| WO | WO 2011005355 | 1/2011 |
| WO | WO 2012031298 | 3/2012 |
| WO | WO 2012154204 | 11/2012 |
| WO | WO 2014160649 | 10/2014 |

OTHER PUBLICATIONS

Mast Y, Wohlleben W., "Streptogramins—two are better than one!" Int J Med Microbiol. Jan. 2014;304(1):44-50 (Epub Sep. 4, 2013).*
Warmus, JS, et al., "Structure based design of an in vivo active hydroxamic acid inhibitor of P. aeruginosa LpxC," Bioorganic & Medicinal Chemistry Letters, Feb. 16, 2012, vol. 22, pp. 2536-2543.
Liang, X, et al., "Synthesis, structure, and antibiotic activity of aryl-substituted LpxC inhibitors," J. Medicinal Chemistry, Aug. 5, 2013, vol. 56, pp. 6954-6966.
Liang, X, et al., "Synthesis, structures, and antibiotic activities of LpxC inhibitors based on the diacetylene scaffold," Bioorg. Med. Chem., Jan. 15, 2011, vol. 19, pp. 852-860.
Barb, AW, et al. "Mechanism and inhibition of LpxC: an essential zinc-dependent deacetylase of bacterial lipid A synthesis," Curr. Pharm. Biotechnol., Feb. 2008, vol. 9, pp. 9-15.

* cited by examiner

*Primary Examiner* — Thomas S Heard
(74) *Attorney, Agent, or Firm* — Monique Vander Molen

(57) ABSTRACT

New improved formulations comprising a first composition and a second composition, the first composition being a streptogramin, the second composition being an inhibitor of lipid A deacetylase resulting in permeabilization of an outer membrane of a microorganism to which it is provided to. Said composition, alone or in combination may be used to treat bacterial infections, providing better efficacy, bioavailability and or pharmacokinetics as compared with other antimicrobial agents. The combination may be provided independently or together, and via any route(s) and in any formulation or form.

24 Claims, 7 Drawing Sheets

PRISTINAMYCIN COMPOSITIONS, LPXC COMPOSITIONS, THEIR IMPROVEMENTS, AND COMBINATIONS THEREOF

CROSS REFERENCE TO RELATED APPLICATIONS

This application claims the benefit of U.S. Provisional Application No. 61/953,721 filed Mar. 14, 2014, the entirety of which is incorporated herein by reference.

BACKGROUND

The invention describes improved compositions and combinations having improved activity and efficacy as antibacterial agents.

Pristinamycin is a streptogramin antibiotic derived from the actinomycete *Streptomyces pristinaspiralis* consisting of two structurally unrelated compounds: group A (pristinamycin IIA) and group B (pristinamycin IA). Group A compounds are polyunsaturated cyclic macrolactones (e.g., streptogramin A, pristinamycin IIA, virginiamycin M and dalfopristin). The group B compounds are cyclic hexadepsipeptides (e.g., pristinamycin IA, virginiamycin S and quinupristin). Pristinamycin entered clinical use as Pyostacine® in 1963. Pristinamycin is used orally for the treatment of multidrug-resistant staphylococci, streptococci, corynebacteria, and *Haemophilus influenzae*. It has very low bioavailability and has, to date, been difficult to provide for other forms of administration. Treatment failures with pristinamycin have been reported. There remains a need to improve bioavailability of this agent, to improve efficacy of the composition, and to administer pristinamycin in other forms.

UDP-3-O-(acyl)-N-acetyl glucosamine deacetylase also referred to as LpxC is an enzyme that catalyzes lipid A biosynthesis in gram-negative bacteria. Inhibition of LpxC has been found to reduce or destroy bacterial pathogenesis. LpxC inhibitors appear to inhibit lipid A biosynthesis and prevent the formation of a complete outer membrane in susceptible bacteria. The efficacy of LpxC inhibitors against many bacteria requires further evaluation. Current LpxC inhibitors are associated with, among other things, safety issues, including cardiotoxicity. There remains a need for improved pharmacokinetics for an LpxC inhibitor, one that is safe for use, and has improved efficacy against more serious bacteria, such as *Pseudomonas aeruginosa*, *Enterobacteriaceae*, *Proteus*, *Haemophilus*, and anaerobic species, including multidrug resistant species, such as cephalosporin and carbapenem-resistant strains.

OVERVIEW

Described herein are new and improved compositions and new uses of said new compositions as described below.

In one or more forms is a first composition as an improved pristinamycin composition, including crystal forms of said first composition and salts of said first composition. The first composition is used as an antibacterial to treat all susceptible infection, including respiratory tract infections, systemic infections, gastrointestinal infections, *Clostridium difficile* infections such as but not limited to pseudomembranous colitis, skin infections, genitourinary tract infections. The first composition may be a streptogramin. The first composition may include a streptogramin A and a streptogramin B. Said first composition may include a formulation having a streptogramin A and a streptogramin B. The ratio of the streptogramin A to the streptogramin B may be from about 90:10 to about 10:90 for the treatment of bacterial infections. The first composition is suitable for bacterial infections susceptible to the combination of the streptogramin A the streptogramin B. In one or more embodiments, the first composition is pristinamycin A to pristinamycin B in the ratio of between about 90:10 to about 10:90. The first composition is suitable for bacterial infections susceptible to the combination of pristinamycin A and pristinamycin B. In some embodiments, the ratio of the streptogramin A to the streptogramin B is at or about 70:30 or between about 60:40 and 80:20. In some embodiments, the ratio of the pristinamycin A to pristinamycin B is at or about 70:30 or between about 60:40 and 80:20. The first composition may be administered orally or as a pro-drug formulation for parenteral (IV) therapy. In one or more embodiments, the first composition is combined with an effective amount of an excipient for oral and/or parenteral administration.

The first composition as an oral or iv formulation provides enhanced streptogramin absorption in order to elevate antibiotic exposure levels (e.g., concentration maximum or Cmax) with or without an effective amount of the excipient. The first composition as an oral or iv formulation may include the pristinamycin A and pristinamycin B in the ratios described above. As the oral formulation, it may be provided as an extended release formulation of pristinamycin to increase antibiotic exposure (e.g., area under the curve or AUC) with or without an effective amount of the excipient. In some embodiments, the first composition in a pharmaceutically acceptable formulation results in a combined increase in exposure as reflected by elevated Cmax and AUC values with or without an effective amount of the excipient.

A first composition may also be delivered by means of inhalation. Said first composition for inhalation is generally provided with an effective amount of an appropriate excipient (e.g., dispersant, carrier, nanoparticle). Delivery by inhalation may be with a nebulizer or a similar device useful for inhalation. In some forms, inhalation therapy will include administration of the new improved first composition as a powder, often as a dry powder. Inhalation may also be in combination with tobramycin, with aztreonam, with tobramycin and aztreonam, with a phosphodiesterase inhibitor (e.g., sildenafil, taladenafil, vardenafil rolipram, etc.), with sodium nitrite or similar or related salts, with sodium nitrite and a phosphodiesterase inhibitor, and any suitable combination thereof. In some embodiments, administration of the first composition may be a combination of an inhaled form along with a systemically administered form of the same drug or another composition (e.g., anti-infective or other pharmacologically active therapeutic agents).

In some embodiments, any formulations of the first composition may be administered in combination with another antibacterial agent or composition, or with another antiviral agent or composition, or with another antifungal agent or composition, or with another anti-parasitic agent or composition, or with another anti-infective agent or composition providing a synergistic effect. The synergistic effect is in part by administration with at least a second composition, the second composition being one that inhibits lipid A deacetylase so as to permeabilize the outer membrane of the susceptible microorganism (e.g., bacteria, virus, etc.).

Described herein is also the second composition, which is one that inhibits lipid A deacetylase. In one or more forms the second composition is an LpxC inhibitor. The second composition may be provided as an antibacterial agent for the treatment of microorganisms susceptible to the second composition, including but not limited to respiratory tract infections, systemic infections, gastrointestinal infections, infections including pseudomembranous colitis, skin infections, and genitourinary tract infections. The second composition may be provided as a pharmaceutically acceptable composition, or salt, or pro-drug, or provided orally, in parenteral or iv form or for administration by inhalation. In one or more forms, the second composition will include an effective amount of an excipient to facilitate parenteral or iv therapy or an effective amount of an excipient to enhance oral absorption or absorption by inhalation. The second composition includes its crystal form, powder form and any salts thereof.

An oral formulation of the second composition is provided with an increased Cmax and/or elevated AUC with or without the effective excipient. Also provided is an oral extended release formulation providing an increased exposure of the second composition over time (e.g. increased AUC) in the absence or presence of an effective amount of the excipient.

The second composition when provided for delivery by means of inhalation is generally provided with an effective amount of an appropriate excipient (e.g., dispersant, carrier, nanoparticle). Deliver by inhalation may be with a nebulizer or a similar device useful for inhalation. In some forms, inhalation therapy will include administration of the second composition as a powder, often as a dry powder. Inhalation may also be in addition with tobramycin, with aztreonam, with tobramycin and aztreonam, with a phosphodiesterase inhibitor (e.g., sildenafil, taladenafil, vardenafil rolipram, etc.), with sodium nitrite or similar or related salts, with sodium nitrite and a phosphodiesterase inhibitor, and any suitable combination thereof. In some embodiments, administration of the second composition may be a combination of an inhaled form along with a systemically administered form of the same drug or another composition (e.g., anti-infective or other pharmacologically active therapeutic agents).

In some embodiments, any of the second compositions described herein may be administered in combination with another antibacterial agent or composition, or with another antiviral agent or composition, or with another antifungal agent or composition, or with another anti-parasitic agent or composition, or with another anti-infective agent or composition.

Further described herein is a new formulation comprising the first composition in combination with the second composition. Said combination may be used for any one or more microorganisms susceptible to both the first and second composition or susceptible to at least one of the first and second composition. Said combination will in one or more embodiments behave synergistically, providing a broad spectrum effect with better efficacy and bioavailability than many other broad spectrum agents. Also described are the first and second compositions described herein in addition to other agents, in suitable variations or variants thereof, particularly including a combination or the first composition described herein and the second described herein via the route(s) described herein. Said first and second compositions may be co-administered (concomitantly) or in series. Said first and second compositions may be delivered in one formulation comprising both compositions or by co-administration, concomitantly or in series. Said combination of the first and second compositions described herein may include a phosphodiesterase inhibitor for inhalation. Said combination of the first and second compositions described herein may include sodium nitrite for inhalation.

BRIEF DESCRIPTION OF THE DRAWINGS

For a more complete understanding of the description provided herein and the advantages thereof, reference is now made to the brief description below, taken in connection with the accompanying drawing and detailed description.

DETAILED DESCRIPTION

Figure 1A:
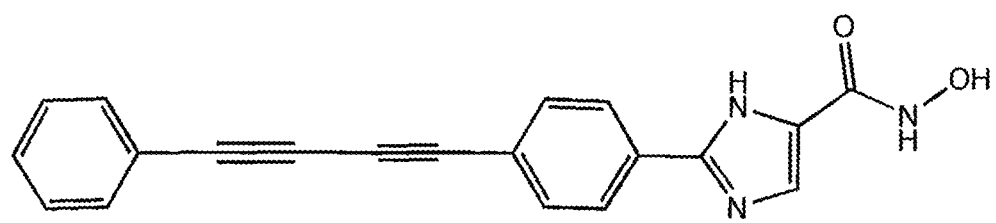
FIGS. 1A to 1J illustrates various representative second compositions.
Figure 1B:
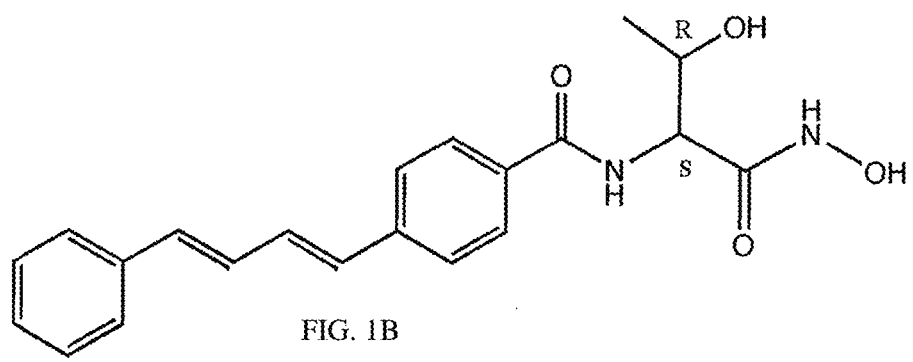
Figure 1C:
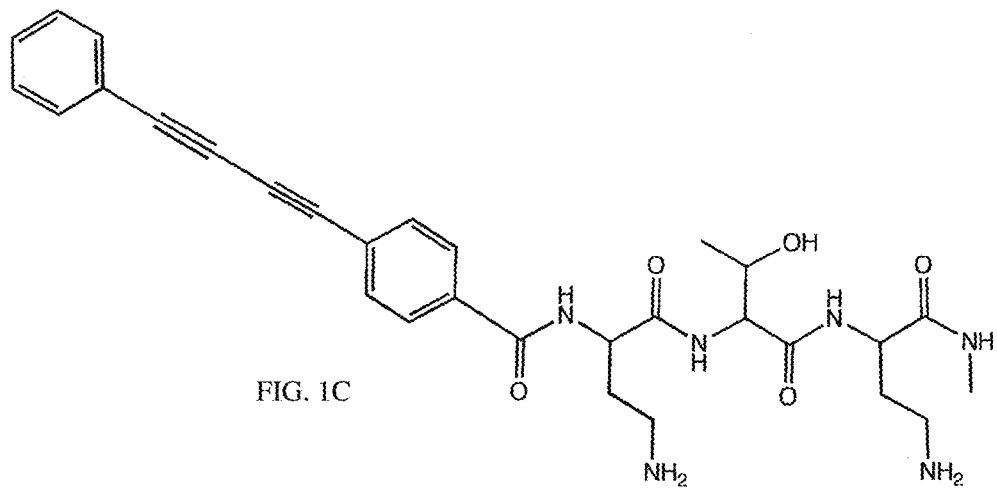
Figure 1D:
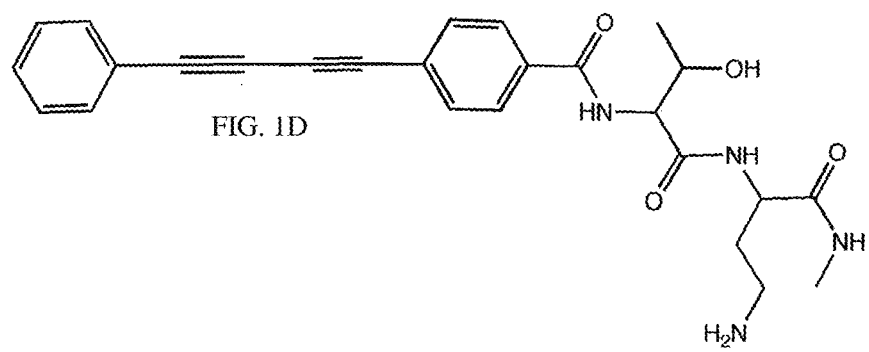
Figure 1E:
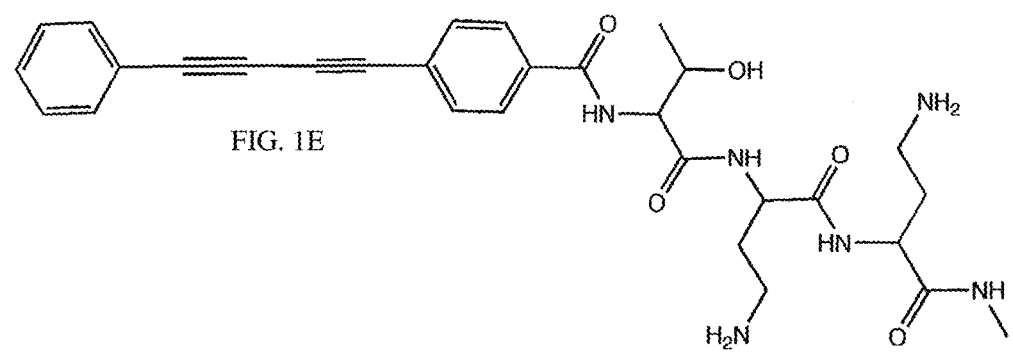
Figure 1F:
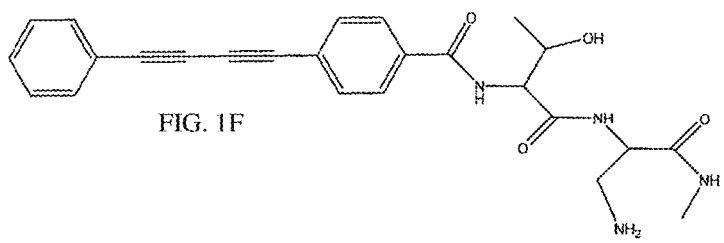
Figure 1G:
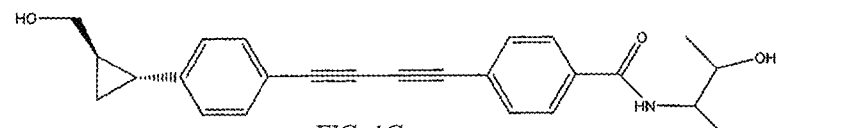
Figure 1H:
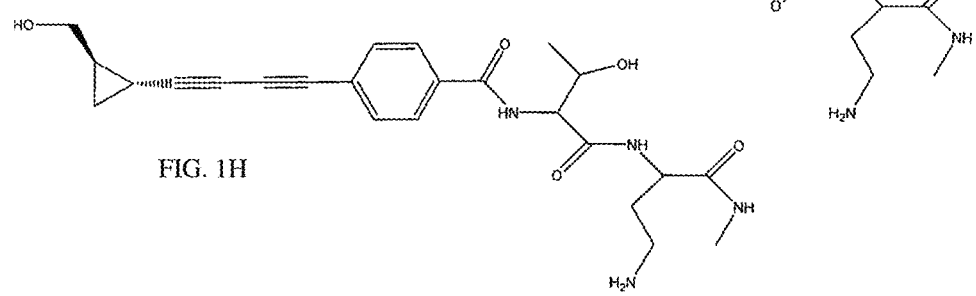
Figure 1I:
Figure 1J:
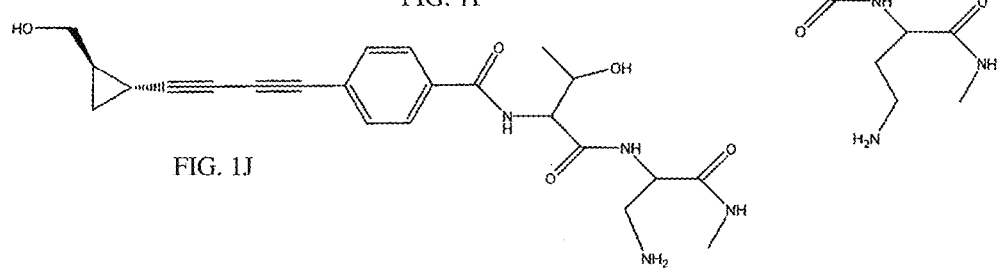

Although making and using various embodiments are discussed in detail below, it should be appreciated that as described herein are provided many inventive concepts that may be embodied in a wide variety of contexts. Embodiments discussed herein are merely representative and do not limit the scope of the invention.

A first composition is described which is a streptogramin. The steptogramin will have two components, streptogramin A and streptogramin B. One representative example is pristinamycin made of two individual components, each having bacteriostatic activity although the A component, shown as formula (I) appears to be the primary driver of all antibacterial activity as compared with the B component, shown as formula (II). In combination, pristinamycin (A and B together) has bactericidal activity.

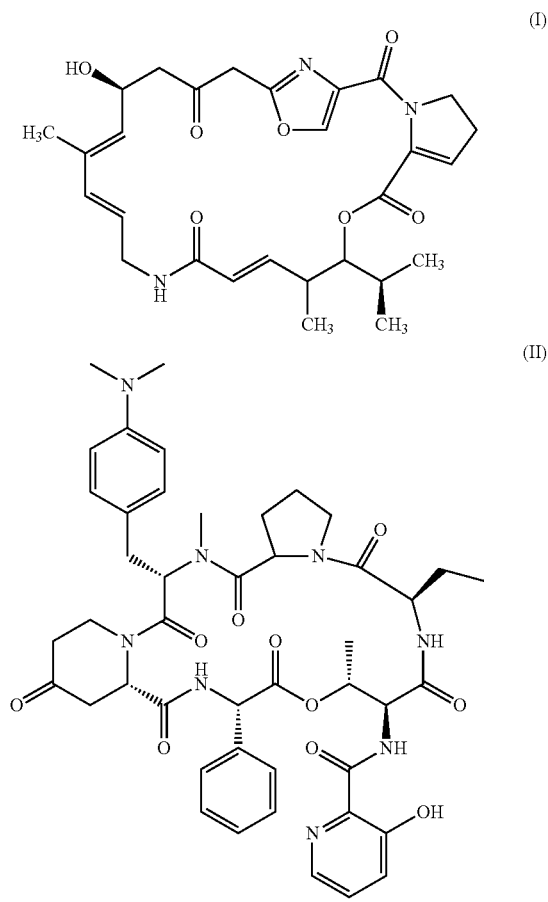

As described herein, the steptogramin, such as pristinamycin, includes any comparable derivative or synthetic so-called equivalents. A primary consideration for the first composition is that it not be administered in conjunction with colchicine due to associated mortalities having been described. The mechanism of action is unclear with respect to this contraindication. General and conventional anti-infective considerations also include potential hypersensitivities.

By prolonging the time at or near the $C_{max}$, the duration of antibiotic exposure with regard to the first composition will potentially increase resulting in an increase in efficacy. For example, pristinamycin administered orally at 120 mg/kg either once, or divided into 2 doses spaced approximately 3 hours apart show the parameters in TABLE 1.

TABLE 1

| Parameter | 120 mg/kg single | 120 mg/kg split |
|---|---|---|
| $C_{max}$ blood | 4.92 µg/mL | 4 µg/mL |
| $T_{max}$ blood | 0.5 hr | 3.5 hr |
| Duration | 8 hr | 8 hr |
| $C_{max}$ lung | 3 µg/mL | 2.03 µg/mL |
| $T_{max}$ lung | 0.25 hr | 4 hr |
| Duration | 2 hr | 4 hr |

Thus, as described herein, by prolonging the time at or near the Cmax, the duration of exposure of the first composition described herein will increase, resulting in an increase in efficacy.

Provided herein are various formulations of the first composition, such as when provided as the pristinamycin, including, for example, a 250 and 500 mg form, which may further comprise a film coating composition and an excipient, and optionally a colorant. The formulations may be immediate release or delayed release formulations, e.g., fast-released, controlled, sustained, or delayed-release. The excipient is a compendial (USP/NF/Ph.Eur.) grade. Any colorants are certified by its supplier to meet the current Color Additive Regulations for both the EU and US. Said compositions are manufactured for increased oral bioavailability, having an increased dissolution rate of the active components, thereby providing improved efficacy. The first composition is manufactured by one or more of drug layering, hot-melt extrusion, and lipid drug delivery.

Manufacturing of formulations for the first composition for oral administration as described herein will include mixing, granulating (aqueous or non-aqueous), de-lumping, drying, milling, lubricating and tabletting, followed by film coating. The tablets to be produced will exhibit satisfactory chemical and physical stability, dissolution profiles, and batch-to-batch consistency. Alternatively dry granulation (e.g., roller compaction or direct compression; mixing followed by compression) can be used for providing various composition strengths. The dry granulation form is likely to provide enhanced stability outcome. When packaged, the packaging will include an induction-sealed opaque high density polyethylene bottle with plastic cap. Said packaged compositions should maintain their physical and chemical stability for up to 2 years when stored at or about 25° C. (at or about 77° F.), with variations ranging from about 15°-30° C. (about 59°-86° F.). Hard gelatin or soft gelatin capsules are also contemplated, using known methods.

A representative coating is an aqueous film coating containing several excipients required for film coating. For example, one coating system is a hydroxypropyl methylcellulose-2910 (6 cps) as a film former, talcum as a glidant, titanium dioxide as an opacifier, triacetin as a plasticizer, and yellow and red iron oxides as colorants, which are certified by the supplier to meet the current Color Additive Regulations for both the EU and US. Any such film coat is one having good adherence to the surface of the formed composition, thereby masking any possible taste. The film coat shall, moreover, ease swallowing of the tablet and ensure safe handling of the product.

To evaluate the safety, efficacy, and pharmacokinetics (PK) of the first composition, such as when provided as pristinamycin, one or more of the following can be evaluated, as representative examples: for the treatment or improvement of the acute bacterial skin and skin structure infections (ABSSSI); for the treatment or improvement of osteomyelitis/prosthetic joint infections; for the treatment or improvement of sexually transmitted infections, such as *chlamydia*, gonorrhea, and ureaplasma; and acne vulgaris For treatment or improvement of ABSSSI, the first composition may be administered with IV vancomycin, with an option to switch to oral pristinamycin. ABSSSI include cellulitis/erysipelas, wound infection, major cutaneous abscess, and burn infection, as defined in an FDA Draft Guidance for Industry on ABSSSI. Less complicated skin infections include minor cutaneous abscess and impetigo. ABSSSI may be caused by streptococci and/or staphylococci, including MRSA. Treatment may include providing initially with IV vancomycin, with a later switch from IV to oral pristinamycin, and/or oral linezolid. Assessment may be based on blood sample collections at predefined time-points (for PK), safety assessments (including clinical laboratory tests, physical examinations, vital signs, and ECGs at predefined time-points) and/or adverse events.

For treatment or improvement of sexually transmitted infections, such as *chlamydia*, gonorrhea, and ureaplasma, the first composition may be administered, such as in a single IM dose. The administration may be alone or in combination with another agent, such as azithromycin (e.g., 1 g orally in a single dose) for 7 days, which will comply with a current CDC recommendation for treatment of uncomplicated gonococcal infections of the cervix, urethra, and rectum.

For treatment or improvement of acne vulgaris, the first composition may be orally administered, such as in a single IM dose for up to 12 weeks or for a minimum of 12 weeks; the latter is one recommendation by the FDA.

A second composition is also described. The second composition is provided with the first composition exhibiting in combination a synergism. Without being bound by theory, synergism is believed to include specific activity of the second composition which inhibits lipid A deacetylase activity resulting in permeabilization of the outer membrane of a microorganism which is also exposed to the first composition. Thus, the second composition allows for the microorganism to become susceptible to or sensitized to the first composition, or the streptogramin, such as pristinamycin. The second composition is one that inhibits lipid A deacetylase activity. The second composition may also be referred to as an LpxC inhibitor. The second compositions may be provided in any of a number of formulations, including oral or IV formulations. Various second compositions for oral administration may further comprise a film coating composition and an excipient, and optionally a colorant.

TABLE 3 shows some PK parameters for alternative LpxC inhibitors following IV or PO administration as performed by others.

TABLE 2

| Species | Rat | Rat | Dog | Monkey |
|---|---|---|---|---|
| Dose (mg/kg) | 5 | 50 | 5 | 1 |
| Route | IV | PO | IV | IV |
| $C_{max}$ (µg/mL) | NA | 4.9 | NA | NA |
| $T_{max}$ (hr) | NA | 0.38 | NA | NA |
| AUC (µg * h/mL) | 1.4 | 7.7 | 0.8-2.5 | 0.31 |
| CL (mL/min/kg) | 60 | NA | 33-105 | 53 |
| Vss (L/kg) | 2 | NA | 3.7-3.9 | 1.5 |
| $T_{1/2}$ (hr) | 1.6 | 1.3 | 1.7-6.8 | 0.67 |
| F (%) | NA | 55 | NA | NA |
| % Urinary Excretion | 29 | NA | 0.44-1.7 | 0.06 |

The second composition described herein will provide improvements to at least some of the PK parameters shown in TABLE 3.

The second composition described herein will include a structure as depicted in formula (III).

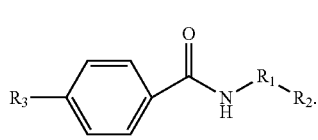

(III)

Various representative structures are depicted in FIGS. 1A to 1J, in which:

R1 and/or R2 may include, for example, any one or more of the following, depicted as

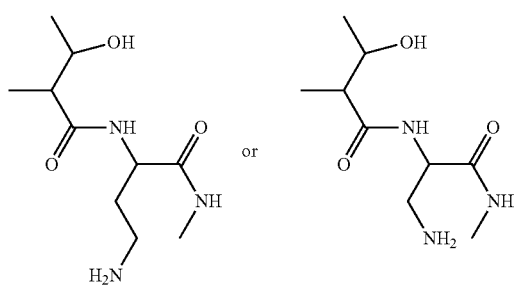

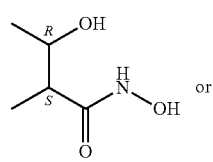

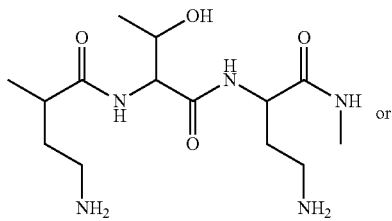

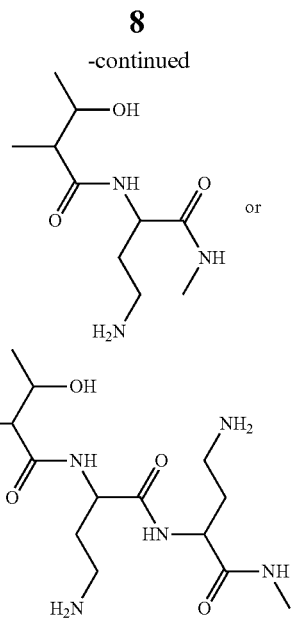

R3 may include, for example, any one or more of the following

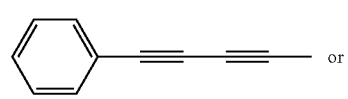

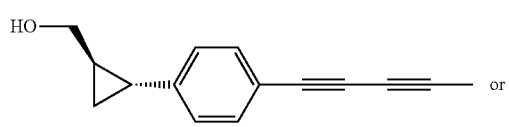

R3 may also include any one or more of R1 and/or R2, alone or in addition to R3 depicted above. For example, the composition may include R3-R2 combinations as well as suitable similar substitutions and/or variations as understood by one of ordinary skill in the art.

The second composition may also include a structure as depicted in formula (IV), in which R1, R2 and R3 are as depicted above or in which R1 is any one or more as depicted below.

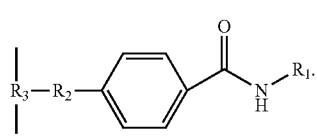

(IV)

The second composition may also include a structure as depicted in formula (V).

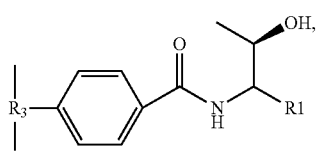

in which R1 is any one or more of

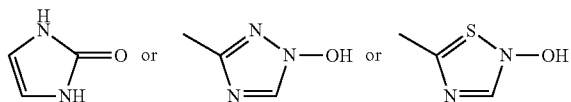

and R3 is any one or more of R3 described above.

Figure 2A:
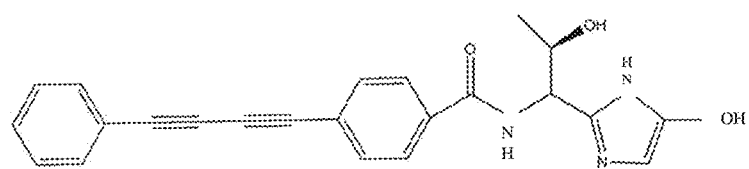
FIG. 2A to 2C illustrates additional representative second compositions.
Figure 2B:
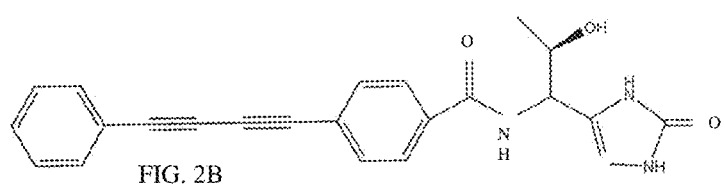
Figure 2C:
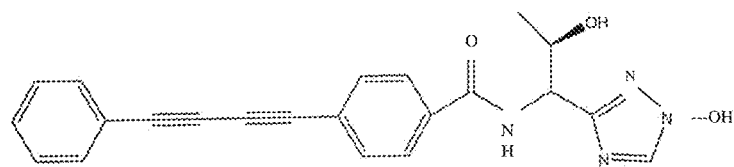

Compositions may also include one or more intermediates, synthetic or otherwise, useful in arriving at and/or making the compositions of formula (I). Representative examples are depicted in FIGS. 2A to 2C. Said intermediates, may, in one or more embodiments, be found as suitable compositions for use as described herein.

Structures of any one or more of formula (I), formula (II), formula (III), and/or formula (IV) and uses of said compositions are also described, including pharmaceutical compositions and acceptable salts thereof. Said compositions may include at least a pharmaceutically acceptable carrier, with or without one or more excipients (e.g., carrier, solvent, adjuvant, diluent). Uses of said compositions may include stabilization, treatment and/or prevention of one or more bacteria susceptible to the compositions described herein. One or more kits containing one or more of the compositions described herein are also included, in which the kits may include instructions and said compositions with or without additional agents, diluents, vials, carriers, etc.

Figure 3:
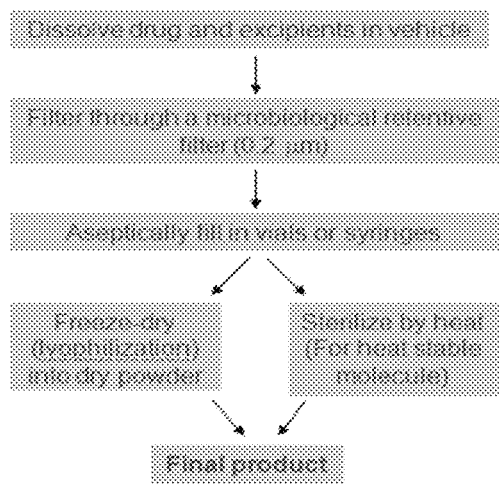
FIG. 3 depicts a representative manufacturing process for an injectable described herein.
Figure 4:
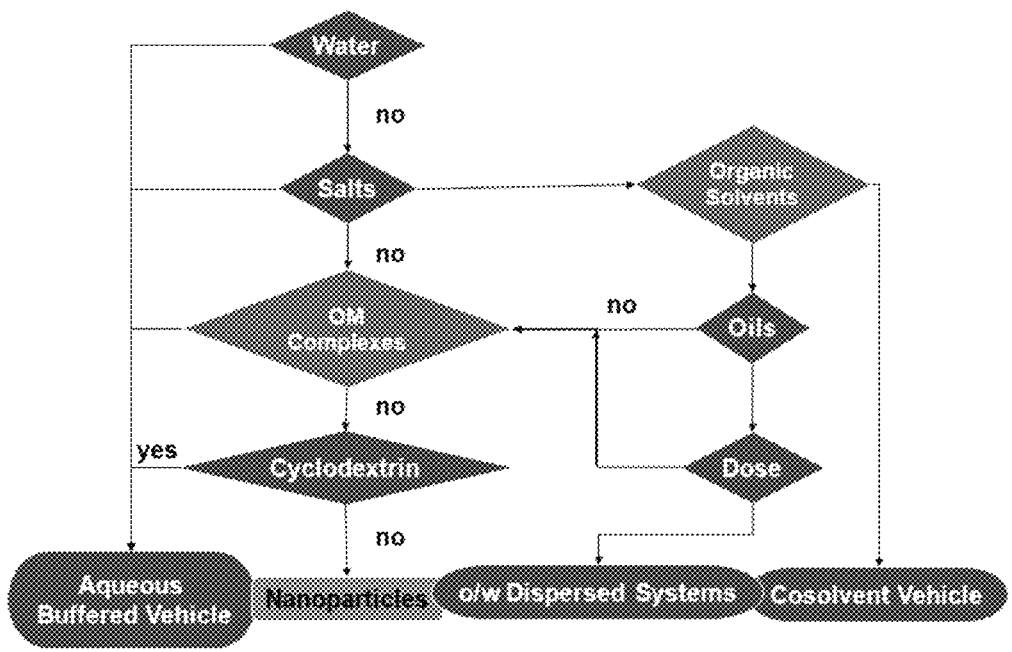
FIG. 4 depicts a representative formulation strategy for an injectable described herein.
Figure 5:
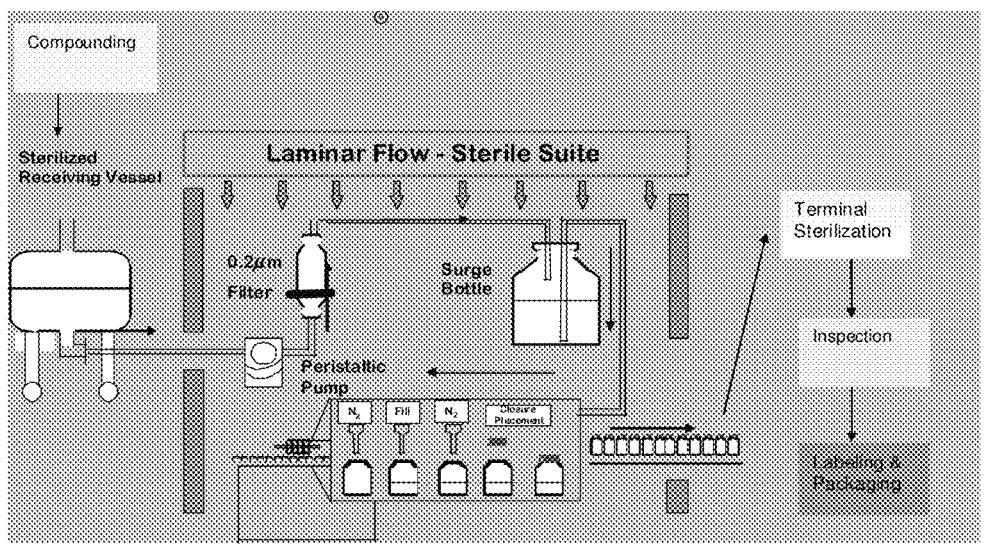
FIG. 5 depicts a representative sterilization process for an injectable as described herein.

When the second composition described herein is provided as an injectable, a suitable manufacturing process is illustrated in FIG. 3. The second composition will generally include an effective amount of an excipient. The excipient will have one or more of the following functionalities: soluble; stabilization (e.g. antioxidant); anti-microbial preservation; impart tonicity (with a goal of achieving isotonicity); bulking agent. A representative formulation strategy is illustrated in FIG. 4. A representative sterilization process is provided in FIG. 5. When formulated, the second composition will, in one or more embodiments, be available in a sterile, pyrogen-free solution or as a lyophilized powder for reconstitution. With single-use vials, they may be supplied either as a frozen solution containing an amount, such as 25 mL, of formulated product in USP Water for Injection or as a lyophilized powder, such as in an amount that will be reconstituted with 23.6 mL of 5% dextrose injection (d5W) prior to intravenous administration. In some embodiments, each mL of formulated solution will also contain 10 mg of active solubilized drug in 100 mg of a suitable solvent, sugar (35 mg dextrose monohydrate for frozen or 12.5 mg mannitol for lyophilized), and either sodium hydroxide or hydrochloric acid for pH adjustment.

A representative manufacturing instruction includes the following: (a) dissolve in suitable solubilizer and either dextrose or mannitol into Water for Injection (WFI) USP grade; (b) add the required amount of active into the solution prepared in step 1; (c) measure the pH of the final solution and adjust to pH 4.5 with 1N HCl or 1N NaOH, as needed; (d) sterile filter the final solution through a 0.22 micro filter into depyrogenated glass vials; (e) for frozen configuration, stopper and cap the vials and place into a freezer at −20° C.; (f) for lyophilized configuration, lyophilize the drug product, stopper and cap the vials and store at 2-8° C. When manufactured under cGMP conditions, the improved compositions will be sterile filtered into depyrogenated clear glass vials (e.g., 30 mL).

The second composition, as the active ingredient, should have at least some of the specifications listed in TABLE 3.

TABLE 3

| Test | Method (Specification*) |
|---|---|
| Appearance | Visual (White to off-white powder free from visual contamination) |
| Identification | Infrared spectrum-KBR dispersion (Conforms to structure) |
| Identification | HPLC (Retention time of sample conforms to that of reference standard) |
| Chromatographic Purity | HPLC Will follow ICH guidelines for reporting impurities (case by case) Report all impurities > 1.0% |
| Chromatographic Assay | HPLC (Report only,% w/w) |
| Water Content | Water Content-Kari Fischer (NMT 10% w/w) |
| Residual Solvents | GC-Headspace (Acetonitrile: NMT 1% w/w) Methyl tert Butyl Ether: NMT 2% w/w) |
| Sulphated Ash | Residual on Ignition: USP (Report only, % w/w) |
| Heavy Metals | Heavy Metals USP (Report only, % w/w) |
| TFA Content | TEA-Content by Capillary Electrophoresis (Report only, % w/w) |

The second composition when finally produced may also have one or more of the specifications of TABLE 4.

TABLE 4

| Test | Method (Specification*) |
|---|---|
| Appearance | Visual (Clear, colorless to slightly colored solution free from visible foreign particulate matter) |
| Identification | HPLC (HPLC retention time of the sample matches that of the reference standard) UV (UV/VIS scan conforms to that of the reference standard) |
| pH | Electrometrically: USP (pH = 4.2-5.2) |
| Volume in Container | USP (NLT 25.0 mL) |
| Osmolality | USP (240-400 mOsm/kg) |
| Chromatographic Assay | HPLC (90-110% of label claim: 10 mg/mL) |
| Chromatographic Purity | HPLC (NLT 85%) |
| Related Substances and Impurities | By HPLC (also by LC/MS) Case by Case following ICH guidelines for determining impurities and degradation in new drug and drug products. |
| Sterility | USP (Sterile) |
| Bacterial Endotoxins | USP (NMT 2.5 EU/mg) |
| Particulate Matter | USP (≥10 um: NMT 6,000/ctn) ≤25 um: NMT 600/ctn) |

The second composition in lyophilized form (e.g., 250 mg/vial) may have the specifications of TABLE 5.

TABLE 5

| Test | Method (Specification*) |
|---|---|
| Appearance of reconstituted solution | Visual (Clear, colorless to slightly pink/amber colored solution essentially free from visible particulate matter) |
| Identification | HPLC (HPLC retention time of the sample matches that of the reference standard) |
| pH (of reconstituted product) | Electrometrically: USP (pH = 4.0-5.5) |
| Chromatographic Assay | HPLC (90-110% of label claim: 250 mg/vial) |
| Chromatographic Purity | HPLC (NLT 85%) |
| Related Substances and Impurities | HPLC |
| Sterility | USP (Sterile) |
| Bacterial Endotoxins | USP (NMT 2.5 EU/mg) |
| Particulate Matter | USP (≥10 um: NMT 6,000/ctn) (≤25 um: NMT 600/ctn) |

Figure 6:
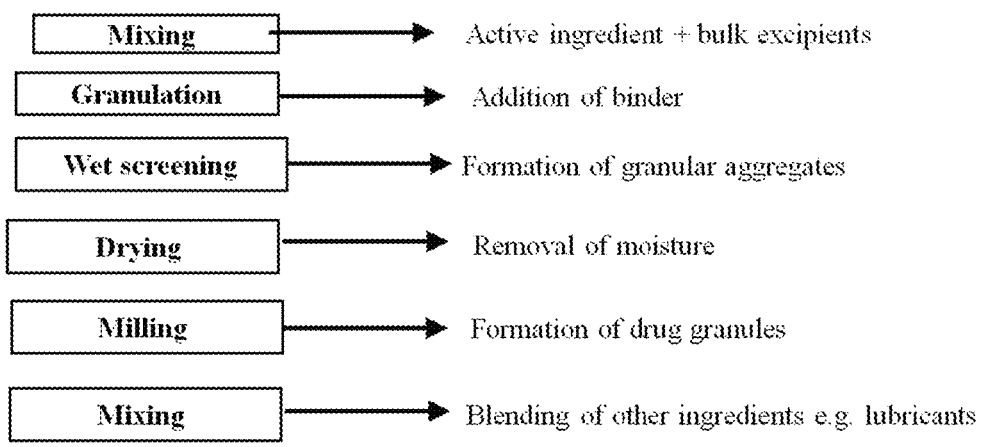
FIG. 6 depicts a representative process for forming a formulation by wet granulation for oral administration.
Figure 7:
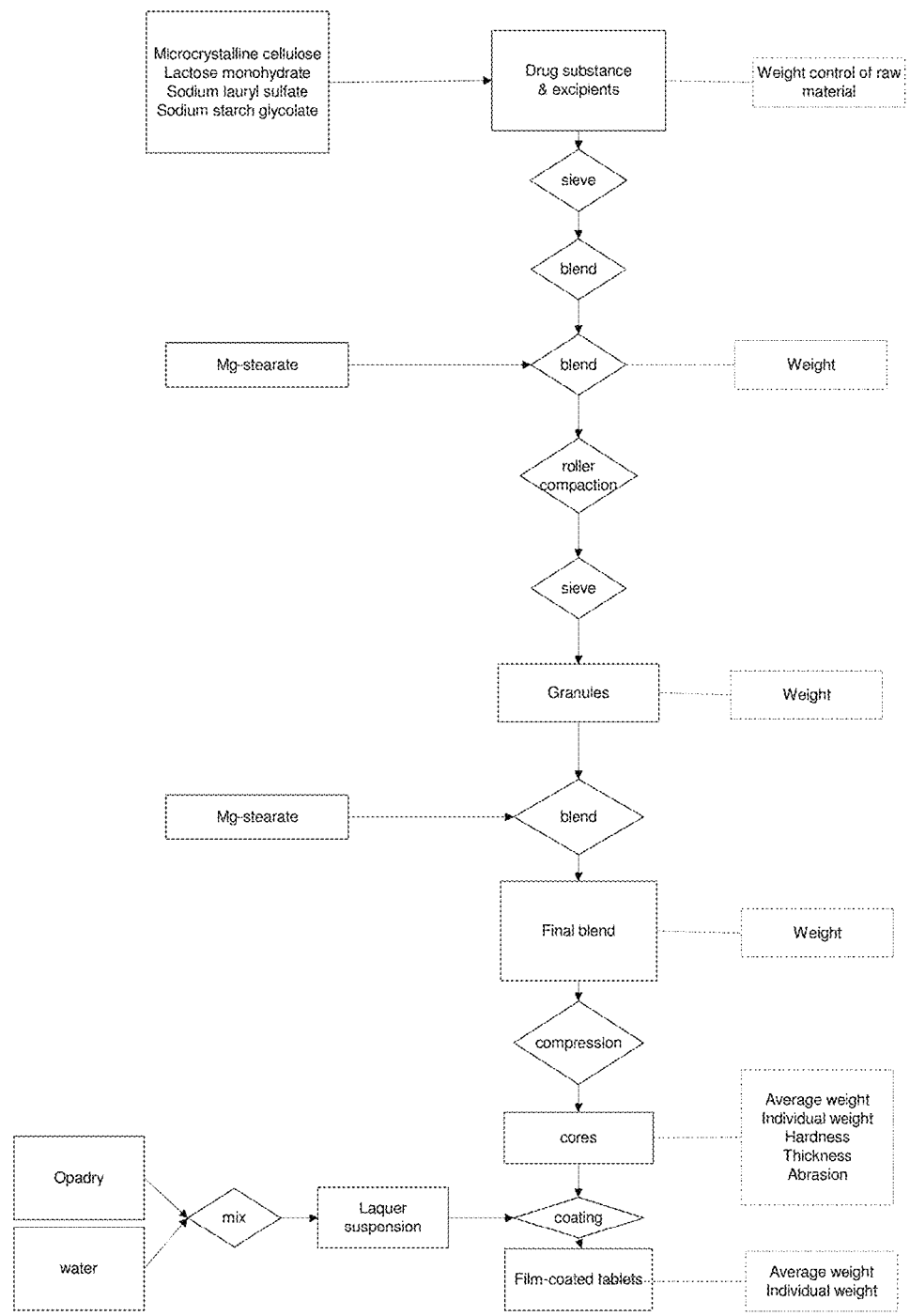
FIG. 7 depicts a representative process for making an oral formulation for dry granulation.

For oral administration of the second composition wet granulation may be considered as one way of manufacturing, when forming tablets. The dry processes may also prove beneficial when the final composition is hydrolytic or heat-sensitive. A representative process for making an oral formulation by wet granulation is depicted in FIG. 6. A representative process for making an oral formulation for dry granulation is depicted in FIG. 7. The final formulation may be for immediate or sustained release (e.g., by layering, such as a multi-layered tablet approach having a different release profile for each layer: fast release in one layer and delayed release in the other(s) which can be modulated to enable the ultimate TPP). A binary combination of the second composition and meropenem can be developed into one multilayered film-coated tablet using such technology. This will have a significant advantage over existing treatments by having a unique oral antibacterial dosage form. This formulation can deliver the active(s) and improve the patient compliance together while achieving anticipated superior efficacy due to the combined effect.

Additional improvements to the first and/or second compositions described herein include increasing the dissolution rate of the active in an oral formulation or tablet combinations, leading to superior efficacy. Examples of these technologies suitable for said improvements include drug layering, hot-melt extrusion (HME) and lipid drug delivery.

A representative HME process includes mixing, kneading, melting, and conveying of materials through precisely controlled temperature zones. The most common twin-screw hot-melt extruder for the pharmaceutical industry is equipped with an intermeshing, co-rotating screw design. This screw design reduces localized overheating of the material, while providing superior mixing, kneading, and conveying throughout the extrusion process. The process is typically conducted without the use of processing solvents, and also significantly decreases the generation of potentially harmful dust. HME can also be employed to produce stable amorphous systems of API(s) and polymer(s). These amorphous systems provide significant benefits including improvements of aqueous solubility, which typically leads to increased drug exposure in vivo. Thus, formulations described herein are prepared by HME (e.g., improved pristinamycin compositions and improved LpxC compositions). HME trials can be carried using the equipment train described below.

While crystalline form of the compositions described are more stable, they may, in one or more embodiments, exhibit poor solubility and poor bioavailability. In some embodiments, amorphous forms of the described compositions will have better solubility, higher dissolution rate, higher bioavailability, and may solve problems related to polymorphic transformation.

Excipients useful for the described HME process (to create said amorphous systems): include but are not limited to polymers, such as acrylic polymers (Eudragit EPO), polyvinylpyrrolidone (PVP K30, PVP-VA, Kollidon VA 64), HPMC (hydropropylmethylcellulose), HPMCAS (hydroxypropyl methylcellulose acetate succinate), poloxamar 188 (nonionic triblock copolymers, Lutrol F68) and polyethylene glycol (PEG). Additionally, the following may be used: lactose hydrous (monohydrate), microcrystalline cellulose (PH 101, 102, 105), sodium starch glycollate (disintegrant), primojel (disintegrant); sodium lauryl sulphate (surfactant), magnesium stearate (tablet lubricant), colloidal silicon dioxide (glidant), talc (anti-adherent) and corn starch (antisticking agent).

A representative procedure includes the following:
1. Calibrated feeder systems.
2. Set the barrel zones to the desired temperatures.
3. Once the barrel zones had equilibrated at the desired temperatures, the screws were engaged.
4. Begin feeding the API (gravimetric feed) and polymer (volumetric feed) [Residence Time: 7 min].
5. The material produced within the first 5 minutes was discarded to ensure adequate distribution during the initial mixing.
6. Collect the extruded intermediate on a conveyer belt, equipped with small fans to assist in cooling.
7. Pass the cooled, hardened intermediate through a pelletizing mill and collected in a poly bag.

A typical or representative HME process combination is illustrated in TABLE 6 below.

TABLE 6

| API (% w/w) | 70 | 70 | 60 | 60 | 80 |
|---|---|---|---|---|---|
| E PO (% w/w) | 30 | 29.65 | 39 | 39 | 19.5 |
| Talc (% w/w) | 0 | 0.25 | 0.5 | 0.5 | 0.25 |
| Silicon Dioxide (% w/w) | 0 | 0.10 | 0.5 | 0.5 | 0.25 |
| Feed Rate (kg/hr) | 2.2 | 2.2 | 2.2 | 5.5 | 6.6 |
| Screw Speed (rpm) | 150 | 120 | 120 | 150 | 100 |
| Feed Temp (° C.) | Ambient | Ambient | Ambient | Ambient | Ambient |
| Zone 1 Temp (° C.) | 100 | 100 | 100 | 100 | 100 |
| Zone 2 Temp (° C.) | 126 | 130 | 131 | 130 | 126 |
| Zone 3 Temp (° C.) | 126 | 130 | 130 | 130 | 125 |
| Zone 4 Temp (° C.) | 126 | 130 | 130 | 130 | 125 |
| Zone 5 Temp (° C.) | 124 | 138 | 130 | 136 | 126 |
| Zone 6 Temp (° C.) | 124 | 138 | 131 | 136 | 125 |
| Zone 7 Temp (° C.) | 125 | 138 | 130 | 135 | 125 |
| Zone 8 Temp (° C.) | 125 | 138 | 130 | 138 | 127 |
| Melt Temp (° C.) | 115 | 123 | 123 | 124 | 117 |

TABLE 6-continued

| | | | | | |
|---|---|---|---|---|---|
| Melt Pressure (psi) | 17 | 20 | 32 | 32 | 42 |
| Motor Amp (%) | 3 | 2 | 14 | 11 | 20 |

Further to the process depicted in TABLE 6, a screw configuration having eight barrel zones with changing screw geometries, including a main feed at or within a first zone and a vent at or within a sixth zone, and a single strand die at the end of the last zone (e.g., a Micro 18/GL 40 D) is suitable for use for an HME process described herein.

Some proposed specifications for oral tablet formulations of the second composition are depicted in TABLE 7.

TABLE 7

| | Representative Internal analytical specification | | |
|---|---|---|---|
| Parameter | 25 mg Tablet | 100 mg Tablet | 150 mg Tablet |
| Shape | round, biconvex | round, biconvex | round, biconvex |
| Diameter | 6.3-6.7 mm | 8.7-9.1 mm | 10.3-10.7 mm |
| Thickness | 3.0-3.6 mm | 4.4-5.4 mm | 4.9-5.9 mm |
| Color | white, off-white, yellow | white, off-white, yellow | white, off-white, yellow |
| Hardness | — | — | — |
| Individual mass (20 tab.) | 103 mg ⊠ 7.5% | 309 mg ⊠ 5% | 463.5 mg ⊠ 5% |
| Average mass (20 tab.) | 103 mg ⊠ 4% | 309 mg ⊠ 3% | 463.5 mg ⊠ 3% |
| Uniformity of mass | corresponds to Ph.Eur. | corresponds to Ph.Eur. | corresponds to Ph.Eur. |
| Uniformity of content | corresponds to Ph.Eur. & USP | corresponds to Ph.Eur. & USP | corresponds to Ph.Eur. & USP |
| Water content | max. 6% | max. 6% | max. 6% |
| Identity test Active | corresponds | corresponds | corresponds |
| Organic Impurities (To be specified) Content per tablet | max. 0.2% max. 0.3% max. 0.3% max. 0.2% max. 0.2% max. 0.6% max. 0.5% je max. 0.2% max 2.0% | max. 0.2% max. 0.3% max. 0.3% max. 0.2% max. 0.2% max. 0.6% max. 0.5% je max. 0.2% max 2.0% | max. 0.2% max. 0.3% max. 0.3% max. 0.2% max. 0.2% max. 0.6% max. 0.5% je max. 0.2% max 2.0% |
| Active as Active | 27.3 ⊠ 10% 25.0 ⊠ 10% | 109.3 ⊠ 10% 100.0 ⊠ 10% | 163.9 ⊠ 10% 150.0 ⊠ 10% |
| Dissolution | Q = 75% after 45 min | Q = 75% after 45 min | Q = 75% after 45 min |
| Microbial quality | corresponds to Ph.Eur. & USP | corresponds to Ph.Eur. & USP | corresponds to Ph.Eur. & USP |

The useful second compositions will have an increase in efficacy. To evaluate the safety, efficacy, and PK of the second composition, one or more of the following can be evaluated: for the treatment or improvement of hospital-acquired bacterial pneumonia (HABP) and ventilator-associated bacterial pneumonia (VABP) caused by LpxC-susceptible antibiotics; for the treatment or improvement of *Pseudomonas aeruginosa*; for the treatment or improvement of Enterobacteriaceae, *Proteus*; for the treatment or improvement of *Haemophilus*; and for the treatment or improvement of anaerobic species, including those multidrug resistant species, such as cephalosporin and carbapenem-resistant strains. Additional uses include but are not limited to Bacteremia, sepsis, and cystic-fibrosis-associated RTIs due to LpxC-susceptible *Pseudomonas aeruginosa*, Enterobacteriaceae, *Proteus*, *Haemophilus*, and anaerobic species, including those multidrug resistant species such as cephalosporin and carbapenem-resistant strains. Also included are intra-abdominal infections due to LpxC-susceptible *Pseudomonas aeruginosa*, Enterobacteriaceae, *Proteus*, *Haemophilus*, and anaerobic species, including those multidrug resistant species such as cephalosporin and carbapenem-resistant strains. Further included are respiratory tract infections and systemic infections originating due to inhalational exposure due to bioweapon pathogens, e.g., *Yersinia pestis*, *Francisella tularensis*, and *Burkholderia cepacia* and related species.

A dosing regimen of the second composition may include, for example, a duration of about seven days and a maximum of about 21 days. A switch to an oral dosing may be permitted after about three to five days. The second composition may be used alone or in a first combination with meropenem. The second composition may also be provided in a second combination with the first composition described herein. Each of said compositions should provide synergistic effects, showing improvements in responsiveness and/or as treatments that are better than either agent alone. In some embodiments, the combination is far better than either agent alone or than predicted. In some embodiments, concomitant linezolid or the described first composition may be provided, such as for Gram-positive coverage. In vitro and in vivo efficacy evaluations include activity against *E. coli, K. pneumoniae*, and *P. aeruginosa* strains A microbiological response includes eradication and/or presumed eradication of the bacteria in question. Eradication is generally an absence of admission pathogen from appropriately obtained specimens. Presumed eradication is generally an absence of material to culture in a patient who has responded clinically.

In one or more embodiments, any of the second compositions described herein will inhibit lipid A deacetylase resulting in permeabilization of the outer membrane of a susceptible microorganisms to which (or one to which it is exposed to). The second compositions are those not associate with cardiotoxicity. The second composition will result in sensitization of said microorganism to streptogramin antibiotics, such as pristinamycin, those that bind to ribosomal RNA and prevent protein synthesis.

For a new broad spectrum agent, a combination of the new improved pristinamycin composition and the new improved LpxC inhibitor composition is provided. Said combination, in view of the pristinamycin composition, will be effective against bacteria, such as but not limited to *Staphylococcus aureus* (MRSA), *Streptococcus pneumoniae*, *Streptococcus pyogenes*, *Haemophilus influenzae*, *Moraxella catarrhalis*, *Legionella pneumophila*, *Chlamydia pneumoniae*, and *Mycoplasma pneumoniae*, among many other important pathogens, including against *Acinetobacter baumanii*, *Burkholderia* spp., and *Pseudomonas aeruginosa*. In addition, bacteria including but not limited to *Acinetobacter baumanii*, *Burkholderia* spp., *Coxiella burnetii*, Enterobacteriaceae including extended spectrum beta-lactamase and/or carbapenemase producing *Escherichia coli*, and *Klebsiella pneumonia*, *Francisella tularensis*, *Haemophilus influenzae*, *Moraxella catarrhalis*, *Legionella pneumophila*, *Pseudomonas aeruginosa*, *Stenotrophomonas maltophila*, and *Yersinia pestis* among many other important pathogens will be targeted because of the addition of the LpxC inhibitor composition. The new improved LpxC inhibitor composition will also be active against bacterial strains of the clinically significant species that are resistant to quinolones, doxycycline, macrolides, clindamycin, cotrimoxazole, beta-lactams, and other classes. The new improved LpxC inhibitor composition, by affecting the outer lipid membrane, will make it possible for new improved pristinamycin composition to enter into the cell.

Oral, IV and inhlational formulations of the combination can be administered in-vivo. The compositions are manufactured as described previously. Efficacy is determined against drug-resistant reference and clinical strains of *Acinetobacter baumanii*, *Burkholderia* spp., *Bacillus anthracis*, *Coxiella burnetti*, Enterobacteriaceae including extended spectrum beta-lactamase and/or carbapenemase producing *Escherichia coli, Klebsiella pneumonia, Enterobacter* spp. *Citrobacter freundii*, and *Serratia marcescens, Francisella tularensis, Haemophilus influenzae, Moraxella catarrhalis, Legionella pneumophila, Pseudomonas aeruginosa, Stenotrophomonas maltophila*, and *Yersinia pesti*, as examples. MIC range, $MIC_{50}$, $MIC_{90}$, FIC, and MIC distributions will determine suitable combinations.

The combination described herein will overcome and address at least one of the following: poor oral absorption; profound food effects; site-specific absorption; sensitivities, such as to formulation composition, particle size, process variables, polymorphic forms, salt forms or hydration state; common ion effect. The combination provides a synergistic effect of the new improved pristinamycin composition and the new improved LpxC inhibitor composition. The combination provides in-vivo efficacy, bioavailability, and/or pharmacokinetics superior to the individual compositions. The combination provides enhanced target access of the poorly penetrating antibacterial pristinamycin component that is primarily active against Gram-positive pathogens an more active against Gram-negative species with more permeable outer membranes like *Haemophilus* spp., (in contrast to the Enterobacteriaceae, and *Pseudomonas* spp.). The combination provides increase survivability against septic shock from the LpxC inhibitor component. The combination provides excellent Gram-positive spectrum and good Gram-negative activity, thereby offering a broadened spectrum, with synergistic potency and better efficacy.

Data associated with antibacterial (MIC) synergy of pristinamycin in combination with the second composition shown in FIG. 1D, depicted as A-24, are provided in TABLE 8. The MIC (in μg/ml) and the fractional inhibitory concentration (FIC) of the combination described are shown against various microorganisms, including gram positive and gram negative bacteria presenting as clinically resistant forms. For FIC, S is synergy; A is additive; and I is indifferent.

TABLE 8

| | MIC (ug/ml) | | | |
|---|---|---|---|---|
| | A-24 | Pristinamycin | FIC | Interpretation |
| *E. coli* ATCC 25922 | 64 | 64 | ND | |
| Combo | 32 | 2 | 0.53 | S* |
| Combo | 16 | 16 | 0.5 | S |
| Combo | 8 | 32 | 0.625 | A |
| *E. coli* 7623 | 64 | 64 | ND | |
| Combo | 32 | 32 | 1 | A |
| *K. pneumoniae* 170S | 128 | >128 | ND | |
| Combo | 64 | 2 | 0.53 | S |
| *K. pneumoniae* 1161486 | 128 | >128 | ND | |
| Combo | 64 | ≤2 | ≤0.515 | S |
| *A. bamanii* 160S | 64 | 128 | ND | |
| Combo | 32 | 4 | 0.53 | S |
| Combo | 16 | 32 | 0.5 | S |

A further example included the second composition of FIG. 1A in combination with the first composition of pristinamycin against *E. coli* 25922, *K. pneumoniae* 170S, *K. pneumoniae* 1161486, or *A. bamanii* 160S, in which the MIC (ug/ml) was 8, >32, 32 and >32 respectively.

In a further example, the second composition of FIG. 1B was provided in combination with the first composition of pristinamycin against *E. coli* 25922, *K. pneumoniae* 170S, *K. pneumoniae* 1161486, or *A. bamanii* 160S, in which the MIC (ug/ml) was ≤0.03, 16, 32 and >32 respectively.

In a further example, the second composition of FIG. 1C was provided in combination with the first composition of pristinamycin against *E. coli* 25922, *K. pneumoniae* 170S, *K. pneumoniae* 1161486, or *A. bamanii* 160S, in which the MIC (ug/ml) was >64, >64, 64 and >64 respectively.

Reference and clinical isolates were generally obtained from known sources, including American Type Culture Collection (Manasas, Va.) or International Health Management Associates, Inc. (Schaumberg, Ill.). Bacteria were cultured in suitable broth, concentrated by centrifugation, and cryopreserved in the same medium, generally containing 20% glycerol by holding at −80° C. Every two weeks a small amount of frozen culture was removed aseptically and streaked on fresh agar plates to act as a working inoculum. Following overnight growth at about 37° C., the plates were wrapped in parafilm and held at about 4° C. Bacteria (4-5 colonies) were then aseptically transferred into broth growth medium for assays as needed.

Minimal inhibitory concentration (MIC) assays were performed in a manner as described for the CLSI broth microdilution assay guideline (see, Clinical Laboratory Standards Institute, 2009, Methods for Dilution Antimicrobial Susceptibility Tests for Bacteria That Grow Aerobically; Approved Standard, Eighth Edition, M07-A8, Vol. 29, No. 2). Antibiotics were dissolved, and then serially diluted in suitable broth across the assay plate in the classical 2-fold geometric format. Antibiotic concentrations in each well at this point were double what the final assay concentration would be. Bacterial inocula were prepared by swabbing several colonies from a fresh agar plate, and resuspending the bacteria to a density that was the 0.5 McFarland turbidity standard (generally close or equivalent to $1\times10^8$ CFU/m)L. The bacterial inocula were diluted in the broth to about $1\times10^6$ CFU/mL, and a suitable amount, e.g., 100 μL was overlayered onto the wells containing the diluted antibiotics. Following incubation as per the guideline, results were recorded as growth or no growth, and the lowest concentration of antibiotic where no growth was observed was declared the MIC.

To assay for synergy of antibacterial combinations, a recognized synergy checkerboard assay, adapted from the CLSI guideline microdilution assay, was utilized (see Eliopoulos, G. M., and Moellering, R. C, Jr., 1996. Antimicrobial Combinations, pg. 330-396. In: Lorian, V. (Ed.), Antibiotics in Laboratory Medicine, $4^{th}$ Ed., Williams & Wilkins; Baltimore, Md.). The first antibiotic was diluted in cation-adjusted Mueller-Hinton broth across the plate along the horizontal axis with each well in a row containing 50 μL of an identical concentration of antibiotic. Along the vertical axis a dilution series of a second antibiotic was dispensed. At this point the drug concentrations are four fold of the final desired working concentration. The bacterial inoculum is prepared as described above for the MIC assay and 100 μL of culture is overlayered onto the combined antibiotic matrix. Following incubation, wells with no growth are noted. The fractional inhibitory concentration, which provides the mathematical definition (as shown below) is calculated to determine whether antibacterial synergy was observed.

FIC=(MIC-*A* combination/MIC-*A* alone)+(MIC-*B* combination/MIC-*B* alone).

Generally, for FIC: Synergy=FIC≤0.5; Additive=FIC>0.5-1; Indifferent=FIC>1-2; Antagonism=FIC>2-4.

Additional information gathered about the synergistic effect of the described composition as a combination therapy may be evaluated by determining bacterial killing effect. This is performed as described above for the checkerboard synergy assay with the exception that the bacterial count in an assay well was determined by plating at the beginning of the experiment, and identifying at the end of incubation for an assay well where growth was inhibited. This has been adapted from both the broth microdilution and the bactericidal assays (Clinical Laboratory Standards Institute (1999) Methods for Determining Bactericidal Activity of Antimicrobial Agents; Approved Guideline M26-A, Vol. 19, No. 18). One additional difference from the guideline assay is that the starting inoculums (e.g., $5 \times 10^5$ CFU/mL as per the MIC assay instead of $1 \times 10^6$ CFU/mL in the guideline minimal bactericidal concentration assay). The value derived was the reduction in bacterial numbers (viability) for the compounds when alone versus the described composition comprising the combined antibiotics.

Synergism is found using the checkerboard microdilution assay, in which synergy is considered as a four-fold reduction in MIC.

Bactericidal synergy was demonstrated by determining the minimal bactericidal concentration. Similarly, in some embodiments, bactericidal synergy is greater than the defined value of ≥$\log_{10}$ change in viable count assessed by a time-kill assay after 24 hours.

The time kill assay is performed sequentially to the checkerboard synergy studies. Fifty milliliter Erlenmeyer flasks containing 10 mL of pre-warmed sterile broth with or without antibiotics are inoculated with bacteria to a starting level of about $1 \times 10^6$ CFU/mL, followed by incubation at 37° C. with shaking (~200 rpm). At various time points, aliquots are withdrawn, serially diluted in antibiotic-free broth medium and 0.1 mL aliquots of each dilution are spread plated on agar plates. Enumeration is by counting colonies after 24-hours further incubation of the plates at 37° C. and calculating the reduction in viable bacteria.

Although representative processes and articles have been described in detail herein, those skilled in the art will recognize that various substitutions and modifications may be made without departing from the scope and spirit of what is described and defined by the appended claims.

The invention claimed is:

1. A composition comprising a combination of a first composition and a second composition, the first composition being a streptogramin, and the second composition being a compound effective in permeabilizing an outer membrane of a susceptible microorganism, the susceptible microorganism being one or more of a Gram positive bacteria and a Gram negative bacteria, the compound being a compound of formula I:

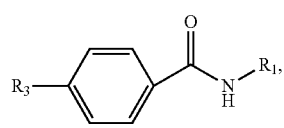

(I)

wherein $R_3$ is any one of:

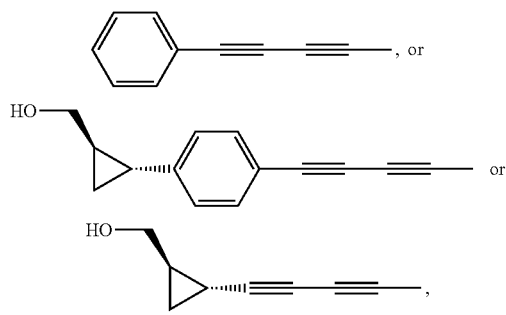

and wherein $R_1$ is any one of:

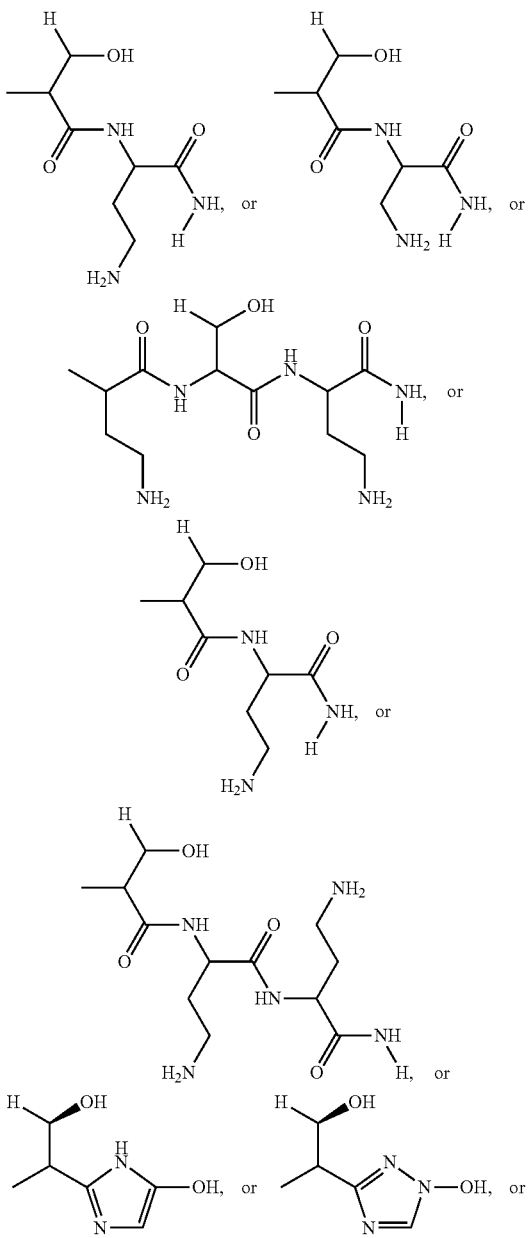

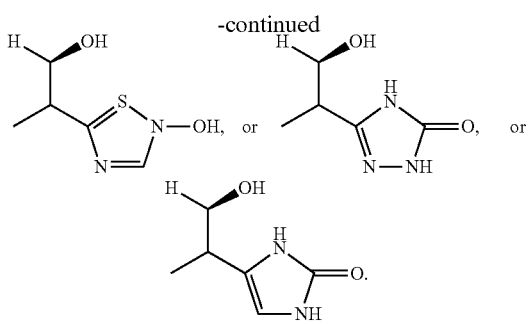

2. The composition of claim 1, wherein the composition comprising the first composition and the second composition is provided as an antibacterial for use against susceptible microorganisms in a subject in need thereof.

3. The composition of claim 1, wherein the composition comprising the first composition and the second composition is provided in a pharmaceutically acceptable form for an IV formulation.

4. The composition of claim 1, wherein the composition comprising the first composition and the second composition is provided with an effective amount of an excipient.

5. The composition of claim 1, wherein the composition comprising the first composition and the second composition is provided in a pharmaceutically acceptable form for an inhalation formulation.

6. The composition of claim 1, wherein the composition comprising the first composition and the second composition is provided in a form for combining with another agent, the another agent including at least one of an antibacterial agent, antiviral agent, antifungal agent, anti-parasitic agent, and anti-infective agent.

7. The composition of claim 1, wherein the composition comprising the first composition and the second composition is provided in a pharmaceutically acceptable form for oral formulation.

8. The composition of claim 1, wherein the susceptible microorganism is one or more of *Staphylococcus aureus*, multi-drug resistant *Staphylococcus aureus*, *Streptococcus pneumoniae*, *Streptococcus pyogenes*, *Haemophilus influenzae*, *Moraxella catarrhalis*, *Legionella pneumophila*, *Chlamydia pneumoniae*, *Mycoplasma pneumoniae*, *Acinetobacter baumanii*, *Burkoholderia* spp., *Pseudomonas aeruginosa*, *Coxiella burnetii*, Enterobacteriaceae including extended spectrum beta-lactamase producing *Escherichia coli* and extended spectrum carbapenemase producing *Escherichia coli*, *Klebsiella pneumonia*, *Francisella tularensis* *Haemophilus influenzae*, *Moraxella catarrhalis*, *Legionella pneumophila*, *Pseudomonas aeruginosa*, *Stenotrophomonas maltophila*, and *Yersinia pestis*.

9. The composition of claim 1, wherein the composition comprising the first composition and the second composition is provided in a pharmaceutically acceptable form with one or more excipient comprising one or more of a pharmaceutically acceptable carrier, solvent, adjuvant and diluent.

10. The composition of claim 1, wherein the composition comprising the first composition and the second composition is provided as an antimicrobial having a broad spectrum of antimicrobial activity, the antimicrobial activity of the composition being better than either the first composition when use alone, or the second composition when used alone.

11. The composition of claim 1 further comprising a phosphodiesterase inhibitor for providing in a form for inhalation.

12. The composition of claim 1 further comprising sodium nitrite for providing in a form for inhalation.

13. A composition comprising an inhibitor of an enzyme involved in lipid A biosynthesis in a susceptible microorganism, the inhibitor resulting in permeabilization of an outer membrane of the susceptible microorganism to which the inhibitor is provided in order to subsequently or concomitantly introduce a streptogramin to the susceptible microorganism, the susceptible microorganism being one or more of a Gram positive bacteria and a Gram negative bacteria, wherein the inhibitor is a compound of formula I:

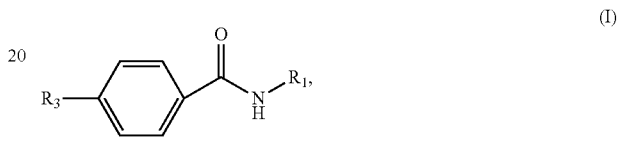

wherein $R_3$ is any one of:

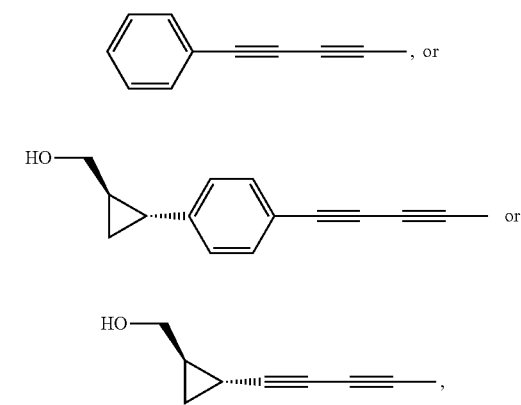

and wherein $R_1$ is any one of:

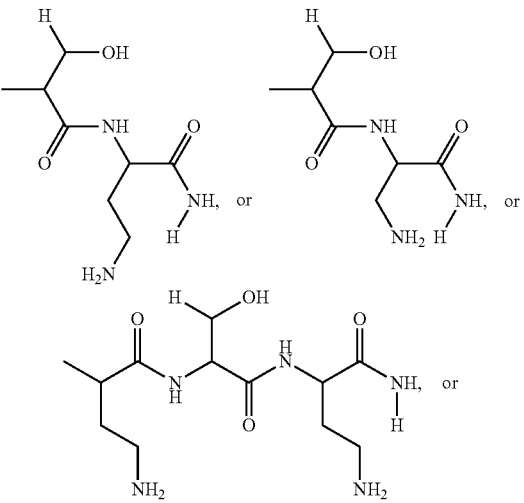

-continued

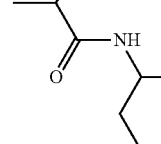

14. The composition of claim 13, wherein the composition is provided as an antibacterial for use against susceptible microorganisms in a subject in need thereof.

15. The composition of claim 13, wherein the composition is provided in a pharmaceutically acceptable form for one or more of an oral formulation, and an IV formulation.

16. The composition of claim 13, wherein the composition comprises an effective amount of an excipient.

17. The composition of claim 13, wherein the composition is provided in a pharmaceutically acceptable form for an inhalation formulation.

18. The composition of claim 13, wherein the composition is provided in a form for combining with a further agent comprising at least one of an antibacterial agent, antiviral agent, antifungal agent, anti-parasitic agent, and anti-infective agent.

19. The composition of claim 13, wherein the susceptible microorganism includes at least one or more of *Escherichia coli*, *Klebsiella pneumonia*, and *Acinetobacter baumanii*.

20. The composition of claim 1, wherein the streptogramin is a combination of a Group A compound comprising a polyunsaturated cyclic macrolactone and a Group B compound comprising a cyclic hexadepsipeptide.

21. The composition of claim 1, wherein the streptogramin is pristinamycin.

22. The composition of claim 13, wherein the streptogramin is pristinamycin.

23. The composition of claim 1, wherein the composition is provided in a pharmaceutically acceptable form for an IV formulation.

24. The composition of claim 13, wherein the composition comprising the first composition and the second composition is provided with an effective amount of an excipient.

* * * * *